United States Patent [19]

Abrahamson et al.

[11] Patent Number: 6,051,567
[45] Date of Patent: Apr. 18, 2000

[54] LOW OXYGEN CONTENT COMPOSITIONS OF 1α, 25-DIHYDROXYCHOLECALCIFEROL

[75] Inventors: Kent Abrahamson, Libertyville; Amy N. Anderson, Waukegan; Haiyan Grady, Mundelein, all of Ill.

[73] Assignee: Abbott Laboratories, Abbott Park, Ill.

[21] Appl. No.: 09/365,533

[22] Filed: Aug. 2, 1999

[51] Int. Cl.⁷ ............................................. A01M 45/00
[52] U.S. Cl. ............................................. 514/167
[58] Field of Search .............................. 514/167

[56] References Cited

U.S. PATENT DOCUMENTS

| | | | |
|---|---|---|---|
| Re. 33,107 | 11/1989 | Dikstein et al. | 514/46 |
| 4,308,264 | 12/1981 | Conway et al. | 424/236 |
| 4,851,221 | 7/1989 | Pak et al. | 424/693 |
| 4,948,788 | 8/1990 | Makino et al. | 514/167 |
| 5,108,767 | 4/1992 | Mulchandani et al. | 426/72 |
| 5,182,274 | 1/1993 | Makino et al. | 514/167 |
| 5,229,422 | 7/1993 | Takahashi et al. | 514/558 |
| 5,529,991 | 6/1996 | Knutson et al. | 514/170 |

FOREIGN PATENT DOCUMENTS

| | | |
|---|---|---|
| 0651994 | 10/1995 | European Pat. Off. . |
| 5238936 | 9/1993 | Japan . |
| 9636340 | 11/1996 | WIPO . |

OTHER PUBLICATIONS

D'Haese, et al., "Contribution of Parenteral and Dialysate Solutions to the Aluminum Accumulation in Dialysis Patients", Blood Purif, vol. 8, (1990), 359–362.

Fleming, et al., "Aluminum Content of Water for Injection Used with Recombinant Human Erythropoietin", Nephrool Dial Transplant, vol. 6 (1991), 857–861.

G.L. Klein, "Aluminum in Parenteral Products: Medical Perspective on Large and Small Volume Parenterals", Journal of Parenteral Science and Tech, vol. 43 (1987), 120–124.

*Primary Examiner*—Theodore J. Criares
*Attorney, Agent, or Firm*—Portia Chen; Gregory W. Steele

[57] ABSTRACT

The invention relates to stable aqueous formulations comprising 1α, 25-dihydroxycholecalciferol, a unit dose system comprising the same in a sealed vessel, and a process for preparing them.

10 Claims, 7 Drawing Sheets

LOW OXYGEN CONTENT COMPOSITIONS OF 1α, 25-DIHYDROXYCHOLECALCIFEROL

TECHNICAL FIELD OF INVENTION

The invention relates to pharmaceutical compositions comprising 1α, 25-dihydroxycholecalciferol, a unit dose system comprising the same in a sealed vessel, and a process for preparing them.

BACKGROUND OF THE INVENTION

The compound 1α, 25-dihydroxycholecalciferol is the active component in a variety of pharmaceutical products having use in treatment of diseases related to abnormal serum calcium level. The compound has the generic name calcitriol, and stimulates intestinal absorption of calcium and phosphorous, making it a beneficial constituent of replacement therapy and treatment of hypocalcemia in patients suffering from a diminished ability to produce or metabolize vitamin D.

1α, 25-dihydroxycholecalciferol is reported in the literature to demonstrate an improved effect on conditions in both children and adults. Use of 1α, 25-dihydroxycholecalciferol includes successful treatment of renal osteodystrophy, hypoparathyroidism, osteomalacia, osteoporosis, hepatic osteodystrophy, vitamin D-resistant rickets, vitamin D-dependent rickets, childhood renal failure and neonatal hypocalcemia. The compound is most widely used in patients with chronic renal failure.

The compound 1α, 25-dihydroxycholecalciferol is known to be sensitive to the presence of oxygen in the form of free molecules and other reactive forms. Sensitivity of the drug manifests itself in the form of producing oxidation-based degradants in solution, resulting in the reduction of potency and a change in solution color. The negative effects tend to manifest themselves even after terminal sterilization and during the shelf life of the product.

To decrease overall oxygen sensitivity of the drug solution, most compositions of 1α, 25-dihydroxycholecalciferol generally employ the use of buffers and/or chelating agents to maintain drug stability as measured by potency and color. See, U.S. Pat. Nos. 4,308,264; 4,948,788; and 5,182,274. The buffer systems and/or chelating agents in such products allow the 1α, 25-dihydroxycholecalciferol solutions to be prepared under less stringent conditions for manufacturing and storage.

However, it has been described that the use of buffers and/or chelating agents is related to certain levels of aluminum in the drug solution. Recently, the Food and Drug Administration has recognized that certain levels of aluminum can be undesirable in pharmaceutical compositions. *Aluminum in Large and Small Volume Parenterals Used in Total Parenteral Nutrition,* Federal Register, FDA, HHS Action: proposed rule 21 CFR Part 201, Jan. 5, 1998. As a result, it is desirable to provide compositions having the lowest levels of aluminum that can be attained. To obtain a low aluminum composition of 1α, 25-dihydroxycholecalciferol, buffers and chelating agents have been removed.

Compositions of 1α, 25-dihydroxycholecalciferol which do not employ the use of buffers or chelating agents are not widely known. Literature recognizing any oxygen stable compositions of such nature has not been described. Pending U.S. application Ser. No. 08/900,981 in the name of Li et al. describes 1α, 25-dihydroxycholecalciferol compositions having low levels of aluminum in solution, which can be achieved in part by removing the buffer and chelating components from the solution. Japanese patent 05-238,936 discloses an aqueous formulation of calcitriol comprising a nonionic surfactant and ascorbic acid. Standard methods of removal or preventing the introduction of oxygen are described, but there is no appreciation of the stringent controls on oxygen limits suitable for preparing a stable low aluminum formulation.

We have now determined that the removal of the buffers and chelating agents from the desired low aluminum formulations diminishes the ability of the composition to compensate for the oxygen-sensitivity of the 1α, 25-dihydroxycholecalciferol active agent and other oxygen-sensitive components of the composition. The presence of oxygen in the 1α, 25-dihydroxycholecalciferol in aqueous formulation predominantly comes from exposure to oxygen in the unfilled area of a container carrying the drug solution (headspace) as well as the absorption of gaseous oxygen into the drug solution.

Commercially available methods for controlling oxygen can achieve an oxygen content level of 3–10% in the headspace. These methods for controlling the oxygen content of the headspace are insufficient for reliably controlling the levels of oxygen necessary to obtain a stable low aluminum formulation of 1α, 25-dihydroxycholecalciferol having desirable potency and color over the shelf life of the composition.

Stringent control of the oxygen levels in the headspace provide beneficial effects for decreasing the total oxygen content in the overall composition, including the container headspace and the dissolved oxygen that is absorbed into the drug solution. Consequently, purging a sufficient amount of oxygen from headspace of the composition affords an overall more stable formulation of the oxygen-sensitive drug. We have determined that to provide a stable composition of a 1α, 25-dihydroxycholecalciferol formulation, which is essentially free of buffer or chelating agent, the composition should have less than or equal to about 2.0% oxygen by volume when determined relative to the volume of the headspace in the container.

Therefore, one object of the present invention relates to providing a composition of 1α, 25-dihydroxycholecalciferol having low oxygen levels of less than or equal to 2.0% oxygen in the headspace of a container. These oxygen levels are suitable to provide a stable low aluminum formulation having less than or equal to about 1 part per million (ppm) of aluminum that is essentially free of buffer or chelating agent.

Another object of the invention relates to preparing a unit dose system in a sealed vessel comprising an aqueous solution of a therapeutic amount of 1α, 25-dihydroxycalciferol having oxygen levels less than or equal to 2.0% oxygen in the headspace.

Yet another object of the invention relates to a process for preparing compositions of 1α, 25-dihydroxycholecalciferol having an amount of less than or equal to 2.0% oxygen in the headspace of a container. Preferably, the container is a unit dose vial.

SUMMARY OF THE INVENTION

In one aspect, the invention relates to a composition comprising a therapeutically effective amount of 1α, 25-dihydroxycholecalciferol in an aqueous solution having less than or equal to 2.0% oxygen in the headspace of a container when determined immediately after container sealing, said solution consisting essentially of a solubilizing agent and an antioxidant. The compositions provide a stable low aluminum formulation having less than or equal to about 1 ppm of aluminum during the shelf life of the composition. The composition is essentially free of buffer and/or chelating agents.

In another aspect, the invention relates to a unit dose system comprising an aqueous solution of a therapeutically effective amount of 1α, 25-dihydroxycholecalciferol in a sealed vessel having an amount of oxygen less than or equal to 2.0% oxygen in the headspace when determined immediately after sealing, said solution of 1α, 25-dihydroxycholecalciferol consists essentially of a solubilizing agent and an antioxidant.

Yet another aspect of the invention relates to a process for preparing a low aluminum composition of aqueous 1α,25-dihydroxycholecalciferol, comprising the steps of:

a. flushing an empty container in the presence of an inert gas, b. maintaining an inert gas environment by filling an aqueous solution of 1α, 25-dihydroxycholecalciferol into said container while consistently flushing with an inert gas, c. suitably minimizing the re-introduction of oxygen during steps (a) and (b) above and during transport of the container, and d. sealing said container in a manner to minimize the presence of oxygen in the container headspace.

The composition can be prepared in a vial according to steps (a) through (c) as described above; placing an appropriate means of closure into the opening of the filled container in a manner which allows the exchange of gas from an interior side of the container to an exterior side of the container; vacuum treating the container headspace and purging the container headspace with an inert gas; and repeating the vacuum treating and purging step to control oxygen content in the container headspace before suitably sealing the container.

In an ampoule, the process is carried out according to steps (a) through (d), wherein the manner of sealing the container is known in the art, typically by flame-sealing.

Still yet another aspect of the invention relates to a product made by the process as described above. The product can be characterized by having a therapeutically effective amount of 1α, 25-dihydroxycholecalciferol in an aqueous solution having less than or equal to 2.0% oxygen in the headspace when determined immediately after container sealing, said solution consisting essentially of a solubilizing agent and an antioxidant.

DETAILED DESCRIPTION OF THE INVENTION

1. Definitions

Figure 1:
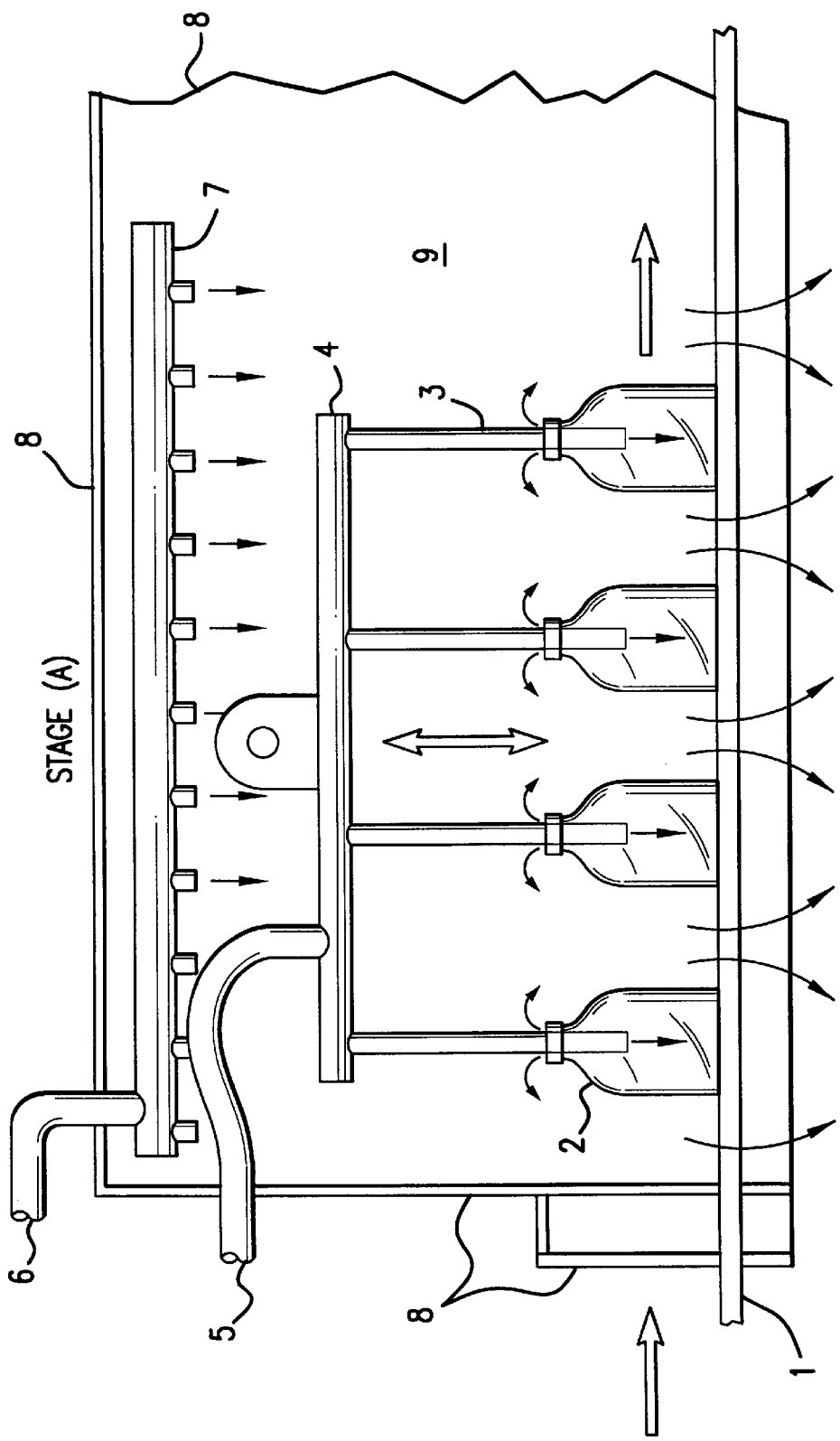
FIG. 1 is a schematic representation of an apparatus suitable for accomplishing preliminary preparation of a suitable container for the composition of the invention, which is described herein and further connoted as Preliminary Processing Stage (A).

As used herein the term "headspace" refers to an unfilled area in a container carrying drug solution. The container is typically sealed to prevent exchange of any gasses present above the filled solution portion of the container with the external gaseous environment outside of the sealed container.

As used herein the term "immediately after container sealing" refers to the period of time before the terminal sterilization step, if a product is terminally sterilized, and after the sealing of the container. In a product that is aseptically filled, the term refers to a reasonable amount of time after the final sealing of the container.

As used herein the term "unit dose system" refers to a pharmaceutical dosage form suitable for a single dose to a patient in need of treatment. Generally, a unit dose system refers to a suitable container, such as a vial or an ampoule, containing a therapeutically effective formulation and a suitable amount of inert gas in the container. One common unit dose system is a unit dose vial. Another common unit dose system is the unit dose ampoule.

As used herein the term "during the shelf life of the product" refers to any point in time during the pharmaceutically accepted term for storing a finished pharmaceutical product. For a 1α, 25-dihydroxycholecalciferol product, the typical shelf life is from about 12 months to about 18 months.

2. Compositions

A composition of the invention will provide an aqueous formulation of 1α, 25-dihydroxycholecalciferol demonstrating improved stability due to controlled levels of oxygen in an amount less than or equal to 2.0% in the headspace of a container. The composition is suitable for parenteral administration. The intravenous route of administration is preferred.

The active agent is 1α, 25-dihydroxycholecalciferol, which is represented by the structure below:

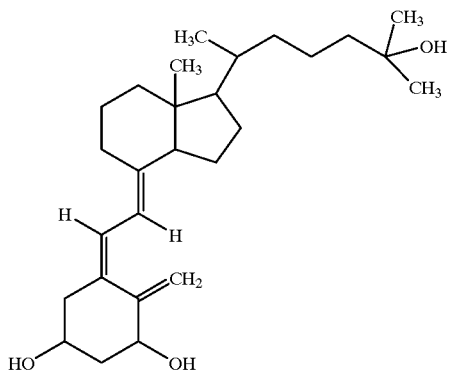

The compound has a molecular formula of $C_{27}H_{44}O_3$, having a molecular weight of about 416.65. The compound is soluble in organic solvents and is practically insoluble in water. Preferably, the active agent comprises from about one to about two micrograms for each milliliter of aqueous solution.

Suitable solubilizing agents for the formulations of the present invention are nonionic surfactants which generally comprise the polyoxalkylene compounds, alcohols, and polysorbate compounds. It is understood by those skilled in the art that the solubilizing agents used in the formulations of the present invention should be of a pharmaceutically acceptable grade and acceptable for administration into humans.

Preferably, the solubilizing agents are selected from dimethylacetamide, polyethylene glycol 400 (PEG 400), polyethylene glyclol 200 (PEG 200), ethanol, isopropanol, 1,3-butanediol, propylene glycol, dimethylsulfoxide, glycerin, polysorbate 20, polysorbate 40, polysorbate 60, and polysorbate 80. In particular, compounds such as polyoxyethylenesorbitan monolaureate and analogous compounds work well due to their solubilizing effectiveness and low toxicity. Other polyoxyethylene ester solubilizing agents which can be used include those listed in, but not intended to be limited to, the 1999 Sigma® Chemical Company catalog. The most preferred solubilizing agent is polysorbate 20.

Generally, the solubilizing agent is used to facilitate the dissolution of the 1α, 25-dihydroxycholecalciferol into solution. Concentrations of the solubilizing agent should be pharmaceutically acceptable and suitable for facilitating the active agent into solution. The suitable amount of solubilizing agent used will depend on the particular agent used in the formulation. It is preferred that the minimum amount of solubilizing agent suitable for dissolving the active agent is used in the composition. Preferably, the polysorbate 20 solubilizing agent comprises at least 0.32% by weight relative to the weight of the drug solution (wt./wt.).

Antioxidants are used to help prevent oxidation of the drug in the product. In the formulations of the present invention, the antioxidant is quickly oxidized thereby minimizing oxidation of 1α, 25-dihydroxycholecalciferol. Exemplary antioxidants include, but are not limited to, water soluble antioxidants. A suitable amount of antioxidant will allow for about 10% to about 20% wt./wt. of the original amount of antioxidant to remain in the composition at the end of shelf life without being consumed. Preferably, the composition comprises from about 0.001% wt./wt. to about 1.5% wt./wt. of the antioxidant, depending on the nature of the antioxidant. Representative antioxidants suitable for the invention are described in Table 1 and are accompanied by a preferred range for each antioxidant.

TABLE 1

| ascorbic acid | 0.01–0.5% | metal ascorbates | 0.2–1.0% |
|---|---|---|---|
| sodium bisulfite | 0.05–1.0% | sodium metabisulfite | 0.025–0.2% |
| ascorbyl palmitate | 0.01–1.0% | sodium sulfite | 0.01–1.0% |
| sodium formaldehyde sulfoxylate | 0.005–0.15% | acetone sodium bisulfite | 0.2% |
| tocopherol | 0.05–0.5% | dilaurylthiodipropionate | 0.01–1.0% |
| thioglycerol | 0.1–0.5% | monothioglycerol | 0.1–0.5% |
| norhydroguaianetic acid | 0.01% | ascorbic acid esters | 0.015% |
| thioglycolic acid | 0.01–1.0% | thiorthodipropionic acid | 0.01–1.0% |

The preferred antioxidants are the metal ascorbates such as the alkali or alkaline earth metal ascrobates. Most preferably, the metal ascorbate is sodium ascorbate (Aldrich Chemical Company, Inc., Milwaukee, Wis. 53233.)

The pH of the formulation can be adjusted by the addition of hydrochloric acid and/or sodium hydroxide. Typically the pH range of the product is from about 5.9 to about 8.5. The more preferred pH is about 7.0.

Compositions of the invention can be supplied in unit dose vials or ampoules, having the headspace filled by an inert gas. Preferably, the containers are protected from light and stored at temperatures from about 15° C. to about 30° C.

It is preferred that the aluminum content of the composition is less than or equal to one part per million (1 ppm). The aluminum content can be determined by atomic absorption spectophotometry and is typically reported in parts per billion (ppb). Preferably, the formulations of the present invention have less than about 1 ppm of aluminum during the shelf life of the product.

A preferred composition comprises 1.0 or 2.0 microgram (mcg) of 1α, 25-dihydroxycholecalciferol, solubilizing agent, antioxidant, hydrochloric acid quantum sufficiat (q.s.), sodium hydroxide q.s., and water for injection q.s. for one milliliter of solution (1 mL).

In a more preferred composition, each milliliter of solution preferably comprises 1.0 mcg of 1α, 25-dihydroxycholecalciferol, 4.0 mg of polysorbate 20, 2.5 mg of sodium ascorbate, hydrochloric acid q.s., sodium hydroxide q.s., and water for injection q.s. Polysorbate 20 is a nonionic surfactant which is commercially available as Tween® 20 (Polysorbate 20, Sigma Chemical Co., St. Louis, Mo., 63178).

Another preferred composition comprises 2.0 mcg of 1α, 25-dihydroxycholecalciferol, 4.0 mg of polysorbate 20, 2.5 mg of sodium ascorbate, hydrochloric acid, q.s., sodium hydroxide q.s., and water for injection q.s. Two examples of the preferred formulations of the present invention are presented below in Table 3.

TABLE 3

| | Solution comprising 1 microgram/milliliter (mcg/ml) of 1α, 25-dihydroxycholecalciferol | Solution comprising 2 microgram/milliliter (mcg/ml) of 1α, 25-dihydroxycholecalciferol |
|---|---|---|
| 1α,25-dihydroxycholecalciferol in polysorbate 20 concentrate, 575 mcg/g | 2.0 milligram/milliliter (mg/ml) | 4.0 milligrams/milliliter (mg/ml) |
| Polysorbate 20 | 2.0 mg/ml | 0.0 mg/ml |
| Sodium Ascorbate | 2.5 mg/ml | 2.5 mg/ml |

TABLE 3-continued

|  | Solution comprising 1 microgram/milliliter (mcg/ml) of 1α, 25-dihydroxy-cholecalciferol | Solution comprising 2 microgram/milliliter (mcg/ml) of 1α, 25-dihydroxy-cholecalciferol |
|---|---|---|
| Hydrochloric Acid | q.s. | q.s. |
| Sodium Hydroxide | q.s. | q.s. |
| Water for Injection | q.s. | q.s. |

3. Process for Making the Composition

Compositions of the present invention can be prepared by a novel process for controlling the total oxygen content in a pharmaceutical composition. In general, an aqueous drug solution containing the desired components in suitable proportions is prepared and transferred in a suitable container via a process for establishing and controlling a low oxygen environment.

In one aspect, the process for establishing and controlling a low oxygen environment comprises the steps of:

a. flushing an empty container with an inert gas, b. maintaining an inert gas environment by filling an aqueous solution of 1α, 25-dihydroxycholecalciferol into said container while consistently flushing with an inert gas, c. suitably minimizing the re-introduction of oxygen during steps (a) and (b) above and during transport of the container, and d. sealing said container in a manner to minimize the presence of oxygen in the container headspace.

The process enables the preparation of a stable, low aluminum composition of 1α, 25-dihydroxycholecalciferol in aqueous solution. The compositions have less than or equal to 2.0% oxygen in the headspace of a container when determined immediately after the container sealing. The oxygen content in the composition is determined volume by volume relative to the total volume of the headspace.

One embodiment of the invention relates to the preparation of a stable, low aluminum composition of 1α, 25-dihydroxycholecalciferol comprising the steps of flushing an empty container in the presence of an inert gas; maintaining an inert gas environment by filling an aqueous solution of 1α, 25-dihydroxycholecalciferol into said container while consistently flushing with an inert gas; suitably minimizing the re-introduction of oxygen during steps the previous steps and during transport of the container; placing an appropriate means of closure into the opening of the filled container in a manner which allows the exchange of gas from an interior side of the container to an exterior side of the container; vacuum treating the container headspace and purging the container headspace with an inert gas; repeating the vacuum treating and purging steps to control oxygen content in the container headspace; and sealing the container in a manner to minimize the presence of oxygen in the container headspace. The preferred container for this embodiment is a vial having a suitable opening for flushing with an inert gas and filling with a solution.

Another embodiment of the invention relates to the preparation of a stable, low aluminum composition of 1α, 25-dihydroxycholecalciferol comprising the steps of flushing an empty container with an inert gas; maintaining an inert gas environment by filling an aqueous solution of 1α, 25-dihydroxycholecalciferol into said container while consistently flushing with an inert gas; suitably minimizing the re-introduction of oxygen during the previous steps and during transport of the container; and flame-sealing the container in a manner to minimize the presence of oxygen in the container headspace. The preferred container for this embodiment is an ampoule.

In step (a), hereinafter the Preliminary Processing Stage (A), a suitable container for the composition of the invention is flushed with an inert gas. A means of conveyance transports the container to a suitable means for flushing the container with an inert gas. The flushing means is connected to a source of inert gas, which is either individually connected to the flushing means or is connected to a plurality of flushing means via a manifold to achieve a suitable flow of gas. The inert gas source typically possesses a quality and purity suitable for use in the manufacture of a pharmaceutical product. The inert gas source can be attached by any suitable means that allows supply of the gas into the flushing means. Preferably, the flushing means is a gassing needle that is connected in such a manner as to allow for the flow of an inert gas into the container. The needle is preferably attached by means consistent with industry practices associated with the maintenance of sterility, quality and purity of the delivered inert gas, container and environment immediately surrounding the container.

Introduction of the inert gas into an empty container displaces previously existing gas contents of the interior of the container through the opening of the container. The typical composition of the displaced gas mixture contains a combination of nitrogen and oxygen. The preferred inert gas for displacing the interior gas contents is nitrogen, which should be of a pharmaceutically acceptable grade.

In step (b), herein after the Filling Stage (B), the container is filled with a desired solution through a suitable filling needle in conjunction with the introduction of inert gas. Preferably, the solution is an aqueous pharmaceutical solution. To obtain a composition of the invention, the drug solution comprises an aqueous solution of 1α, 25-dihydroxycholecalciferol, a solubilizing agent, and an antioxidant as previously described.

It is preferred the container is contemporaneously filled with the drug solution while purging with an inert gas. Nitrogen is the preferred inert gas. The needle can be attached by any means suitable for contemporaneously introducing a solution with an inert gas. Preferably, the needle is attached in a coaxial manner having a solution filling tube and a coaxial flushing tube. Flow parameters of the gas and the solution can be adjusted to minimize the presence of oxygen or any other undesirable gas in the headspace of the container.

To minimize the re-introduction of any undesirable gas in the process, the apparatus for carrying out the Preliminary Preparation Stage (A) and the Filling Stage (B) of the process can be encased under a suitable shroud or enclosure to prevent infiltration of atmospheric gasses into the process environment. An interior volume enclosed by the shroud can be purged with an inert gas, which is preferably introduced via an exterior manifold having outlets extending into the interior volume. The Preliminary Preparation Stage (A) and the Filling Stage (B) can be enclosed under the same shroud or, alternatively, a separate shroud can be fashioned for each stage. When each stage is encased in a separate shroud or enclosure, the containers should be equally protected from undesirable gas introduction, preferably, by means of an enclosure extension, a gassing tunnel or a shroud, which connects between the separate enclosures surrounding the Preliminary Preparation Stage (A) and the Filling Stage (B). Preferably, the extension enclosure or gassing tunnel will be flushed with an inert gas delivered by an attached distribution manifold.

Outlets in the manifolds direct the flow of the inert gas inside of the shroud in a generally downward direction, displacing oxygen or other undesirable gasses within the interior of the shroud. The shroud is equipped with an exit opening, typically located at the bottom of the shroud, which allows displaced gasses to be purged from the interior volume of the chamber. Exemplary outlets in the manifold include holes, jets, needles, and the like or other similar orifices.

The inert gas from the manifold flows down past the container, displacing those gasses which have been purged from the interior of the container during the Preliminary Preparation Stage (A) or the Filling Stage (B). The inert gas, together with any other displaced gasses, will continue down well past and below the container, and exit the shroud or enclosure through a bottom opening. The shrouded environment allows for suitable control over the gaseous environment encased within the shroud and provides an interior atmosphere that is extremely low in any content of undesirable gasses, such as oxygen. It also affords an environment which will minimize or reduce the potential for re-absorption of the oxygen or other undesirable gas into the desired solution previously introduced into the container during Filling Stage (B).

Typically, the process then proceeds in one of two routes. In one route, the container is conveyed to a sealing station. In this route, the container is a suitable vessel having an opening that can be directly sealed by known methods in the art, for example, flame-sealing. A typical container of this kind is an ampoule. In another route, the opening of the container is fitted with a suitable closure, the container and accompanying closure proceed into the sealed chamber for vacuum and purging, which are optionally repeated in succession, and the containers are fully sealed after completion of the vacuum and purging process, preferably inside the sealed chamber. A suitable vessel having an opening that can be sealed upon insertion of the appropriate means of closure is a vial. The vial is the preferred container, which demonstrates the preferred route.

In the preferred embodiment, vials are transported via the means of conveyance and positioned in such a manner that an appropriate means of closure may be inserted, hereinafter the Closure Stage (C). Preferably, the closure is a stopper which is selected in manner as to suit the opening of the vial. A preferred stopper is a vented stopper, which allows the exchange of gas between the interior of the container and the exterior environment of the container (which is coextensive with the interior volume in the shroud). Such a stopper allows exchange of the undesirable gas in the headspace of the container to be displaced by the preferred inert gas in the interior volume of the shroud. During the Closure Stage (C), inert gas is introduced by way of a manifold near the top of the shroud to provide a downward flow of an inert gas, which can escape from an exit opening in the bottom of the shroud, as previously described for the Preliminary Preparation Stage (A) and Filling Stage (B).

The containers of either embodiment can be optionally accumulated and collected to facilitate improved handling, hereinafter the Accumulation Stage (D). The containers are typically transferred to a suitable collecting means. Exemplary collecting means are trays, racks, and the like, or any other device suitable to hold a plurality of containers. The containers can be transferred either automatically or manually into the collecting means. The accumulation process is similarly protected by a shroud or enclosure and flushed with an inert gas as previously described. The shroud is equipped with a suitable access door which can be used to remove the collected containers. Preferably, the access door is fitted with a means to seal any opening that is created between the door and the shroud. Typically, the preferred access door is fitted with a gasket or other similar arrangement to provide a suitable seal.

Drawing a vacuum on the headspace of the container and purging the headspace for any remaining undesirable gas, hereinafter referred to as the Vacuum and Purging Stage (E), substantially removes any remaining undesirable gasses in process environment and in the composition. A suitable apparatus for carrying out the vacuum and purging process consists of a sealed chamber and one or more sealable access doors. Preferably, the chamber is equipped with hinged two access doors. The chamber is fitted with a vacuum source and an inert gas source. The vacuum source preferably comprises a motor, vacuum pump, vacuum regulator, and vacuum gauge, and is connect to the chamber via an external control valve. The inert gas source connects to the chamber also via an independent external control valve. Containers are supported by a suitable means for lifting the containers. The sealed chamber is also suitably equipped with a means for regulating pressure within the chamber. The process can be regulated by any suitable means for controlling all aspects and steps of the process. Preferably, the process is controlled by a programmable logic controller (PLC). In the preferred embodiment, the pressure transducer works in conjunction with a PLC to alternately draw a vacuum inside the chamber and flush the chamber with nitrogen.

The process is monitored to avoid evacuation vacuum levels that asymptotically approach the critical vapor pressure or boiling point of the drug solution. In a typical process of the invention, the vacuum chamber controller or PLC program is streamlined to achieve vacuum levels as close as is practicable to the boiling point of the composition. It is preferred that the environment within the processing chamber is allowed to reach equilibrium after the desired vacuum levels have been achieved and then purged with inert gas to flush the entire interior volume of the vacuum chamber. The single completion of the vacuum and purging steps results in a portion of the original oxygen and other undesirable gasses in the headspace being evacuated from the chamber.

Successive flushing and purging cycles further reduce total concentration of oxygen and other undesirable gasses in the headspace and allow for controlled manipulation of the levels of undesirable gasses, particularly oxygen, in the container headspace. The method results in the compositions being exposed to extremely low levels of oxygen and other undesirable gasses, which have not previously been attained by known methods.

A composition of the invention is preferably treated under a series of vacuum draws and oxygen purges performed within an environment purged of oxygen and other undesirable gasses. The vacuum treatment decreases the potential for re-absorption of oxygen into the composition, resulting in less dissolved or re-absorbed oxygen into the composition.

In the preferred embodiment, the vial containers can be suitably sealed while inside the sealed chamber flushed with inert gas by way of a motive force device coupled to a shaft, which extends into the interior of the vacuum processing chamber and is connected to a supporting platen. Preferably, a tray of containers is loaded onto the supporting platen. The motive force device provides a suitable force to lift the platen toward an appropriate seal or sealing system to bring the containers in position with a corresponding pre-positioned closure, such as a stopper. The pre-positioned closure is sealed into the opening of the container by compressing the container and its corresponding closure. To ensure the integrity of the system, the appropriate seal or sealing system can be employed where the shaft passes through the wall of the processing chamber. The shaft retracts when closure of the containers is complete and the vacuum chamber controller or PLC activates the pressure relief valve connected to the vacuum chamber to allow equalization of pressure inside the chamber. The containers can be removed from the chamber and are suitable for further manufacturing, if desired.

Ampoules can be suitably sealed by flame-sealing, which is a method well known to those in the art of pharmaceutical product manufacturing. The desired benefits of the described process are more effectively utilized in a composition of 1α, 25-dihydroxycholecalciferol in an aqueous solution, wherein the aqueous solution consists essentially of a solubilizing agent and an antioxidant. The benefits are most clearly demonstrated in a low aluminum formulation of 1α,25-dihydroxycholecalciferol prepared in an unit dose vial. However, it is believed the process of the invention can be used to control oxygen content in nearly any pharmaceutical composition or unit dose formulation.

Schematic representations of the process and the apparatus employed in the preferred embodiment of the process appear in FIGS. 1–8. Where a directional arrow is used in the schemata, it is intended that the arrowhead indicate the direction of flow of the inert gas. The process of the invention and a suitable apparatus for carrying out the process can be better understood in context of the following more detailed description of the drawings.

In FIG. 1, which refers to the Preliminary Processing Stage (A), a means of conveyance 1 transports a container 2 to a suitable gassing needle 3. The gassing needle 3 is connected to a manifold 4 which is connected to a suitable source of inert gas 5. Alternatively, each gassing needle 3 is individually connected to the source of inert gas 5. The gas flows from the inert gas source 5 via the manifold 4 to the container 2 to displace gas contents into the interior of the container.

An independent source of inert gas 6 enters the environment exterior to the container via a manifold 7. A shroud 8 encloses an interior volume 9. The interior volume 9 is filled with an inert gas 6 delivered by the manifold 7.

Figure 2:
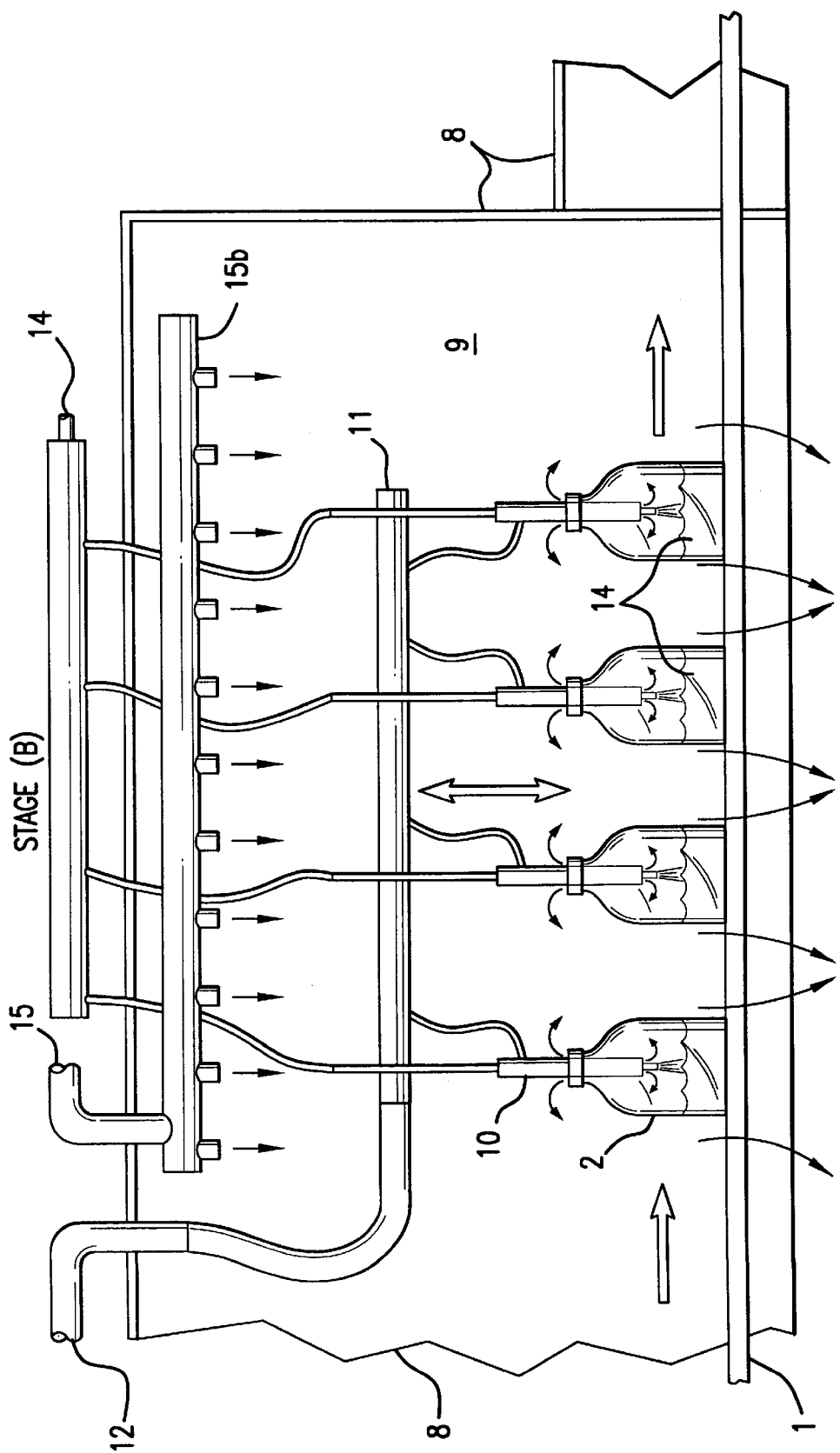
FIG. 2 is a schematic representation of an apparatus suitable for filling suitable container to prepare a composition of the invention, which is described herein and further connoted as the Filling Stage (B).

As illustrated in FIG. 2, which refers to the Filling Stage (B), container 2 is filled with solution via a coaxial filling needle 10. The filling needle 10 is used in conjunction with manifold 11 to supply a source of inert gas 12 while introducing a desired solution 14. The inert gas 12 flows into container 2 via the manifold 11 to purge the gas contents in the interior of the container to the exterior of the container. The apparatus is contained under shroud 8 and the interior volume 9 can be filled with an inert gas. Alternatively, the apparatus is contained under a separate shroud. Gas source 15 flows manifold 15b to purge the interior volume 9 with an inert gas.

Figure 3:
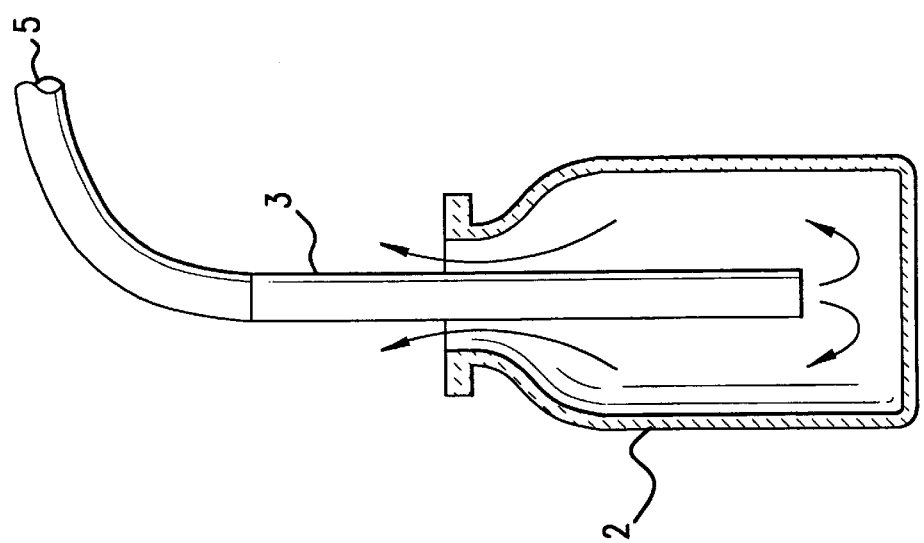
FIG. 3 is a schematic representation of a means of flushing a suitable container to prepare a composition of the invention.

In FIG. 3, the gassing needle 3 feeds the inert gas 5 into container 2. The inert gas flows in the direction of the arrows from the gassing needle 3 into the container 2 and is displaced into the exterior environment of container 2.

Figure 4:
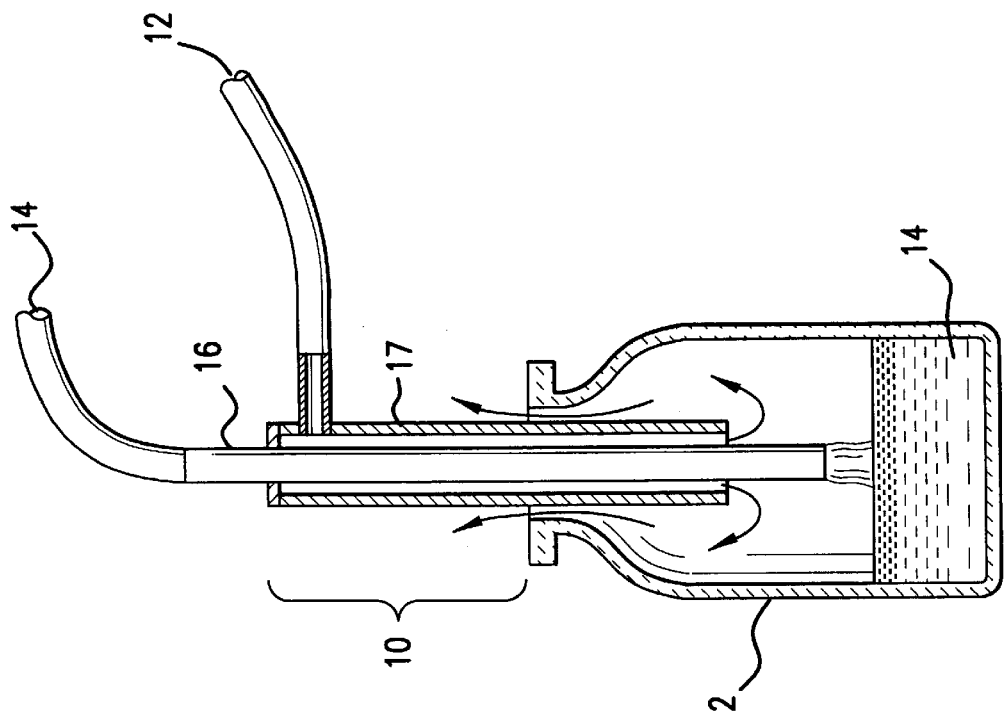
FIG. 4 is a schematic representation of a preferred means for attaching the filling means to prepare a composition of the invention.

According to FIG. 4, the preferred means for attaching the filling needle 10 is by using a coaxial flushing means which comprises a solution filling tube 16 and a coaxial flushing tube 17. Inert gas 12 flows into the headspace of container 2 via the coaxial flushing tube 17, while the desired solution 14 is introduced via filling tube 16.

Figure 5:
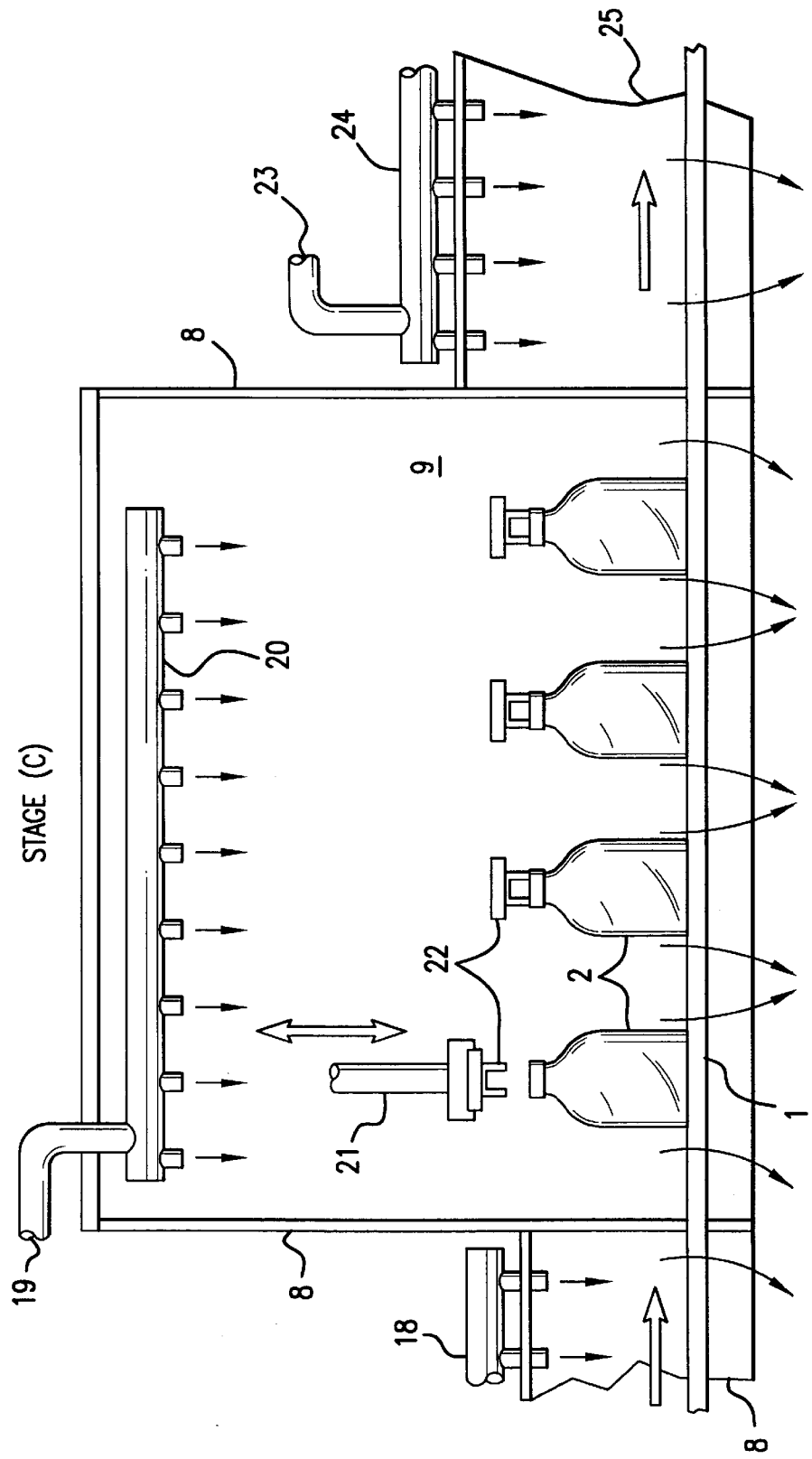
FIG. 5 is a schematic representation of an apparatus suitable for placing a means of closure in a vented position on a container that receives the composition of the invention, which is described herein and further connoted as the Filling Stage (C).

In FIG. 5, which refers to the Closure Stage (C), gassing manifold 18 feeds the inert gas onto and around the container while outside of shroud 8. The means of conveyance 1 brings container 2 to a position that is suitable for receiving via a placing mechanism 21 an appropriate means of closure 22. The means of closure 22 is placed on the container 2 in a manner that will allow the exchange of gas between the interior of the container and the atmosphere outside of the container. The interior environment 9 is filled with an inert gas 19 by means of a suitable manifold 20. The container 2 is conveyed by means 1 to the exterior of the shroud 8. The external environment is protected by a shroud or covered tunnel 25, and purged with an inert gas 23 which is distributed by a manifold means 24.

Figure 6:
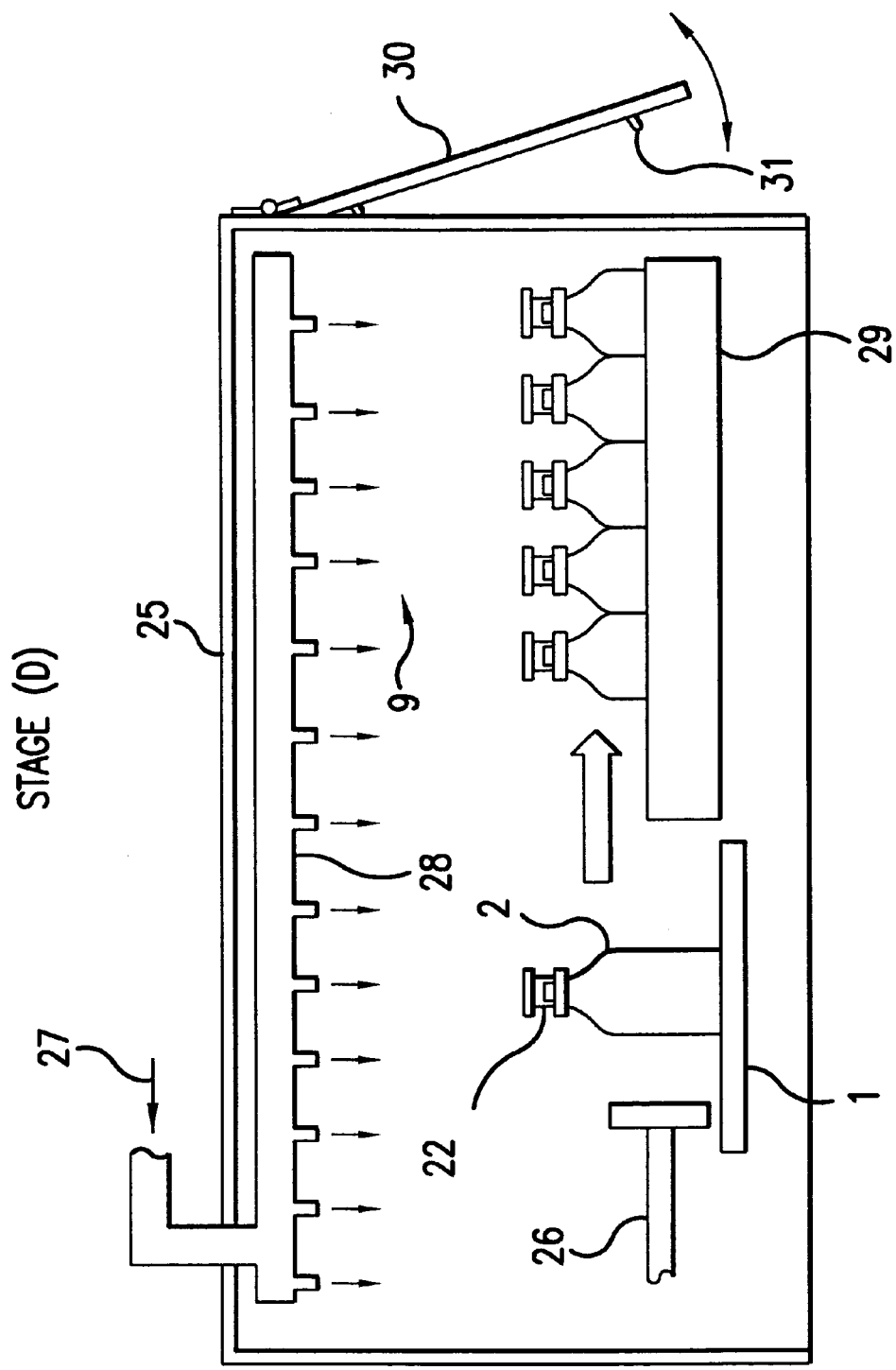
FIG. 6 is a schematic representation of an apparatus suitable for collecting a plurality of containers containing the composition of the invention, which is described herein and further connoted as the Accumulation Stage (D).

As described in FIG. 6, which refers to the Accumulation Stage (D), the container 2 is conveyed by means 1 into the tunnel enclosure 25. A transfer device 26 moves the container 2 in an environment purged by inert gas 27, which is delivered via manifold 28. The container 2 is transferred into a collecting means 29 that can be removed via an access door 30 located at a suitable position in shroud 8. Gasket 31 seals the access door 30 to the shroud.

Figure 7:
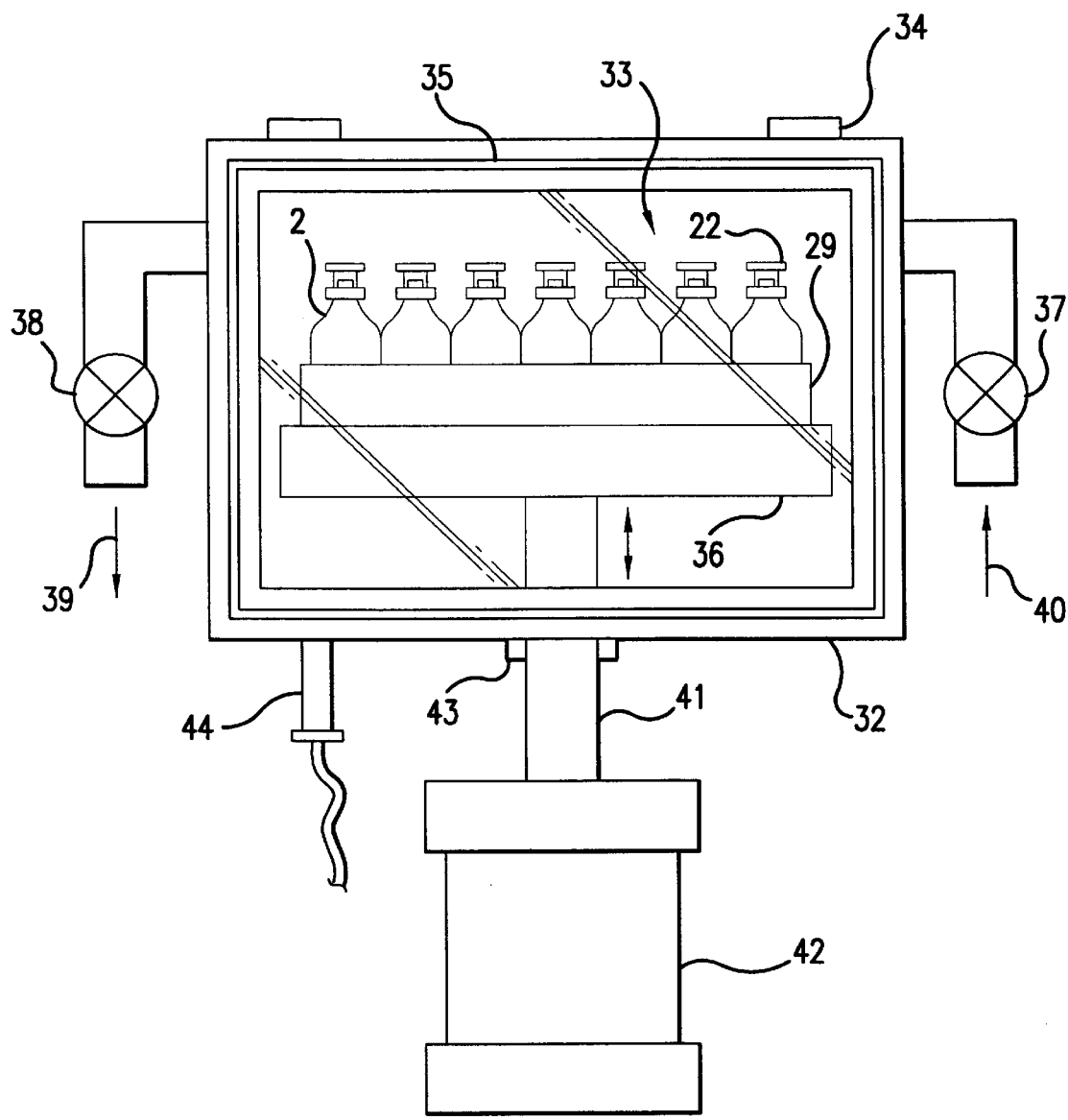
FIG. 7 is a schematic representation of a chamber suitable for drawing a vacuum and purging oxygen from the composition of the invention, which is described herein and further connoted as the Vacuum and Purging Process Stage (E).

As illustrated in FIG. 7, which refers to the Vacuum and Purging Stage (E), sealed chamber 32 is equipped with a gasketed access door 33 connected by hinge 34 and supplemented by gasket 35. A tray of containers is carried by supporting platen 36. Control valves 37 and 38 operate to allow inflow and outflow of the gas and vacuum, respectively, and are attached to the sealed chamber. Vacuum source 39 is attached and controlled by valve 38. An inert gas source 40 is attached to an controlled by valve 37. Shaft 41 extends to the interior of the vacuum chamber and attaches on one end to supporting platen 36. Motive force device 42 couples to the other end of shaft 41 and provides air or hydraulic force to control the movement of supporting platen 36. An appropriate seal or sealing system 43 closes any gap between the shaft 41 and the chamber 32 where the shaft enters the chamber. A pressure transducer 44 is suitably connected to the chamber 32.

Figure 8:
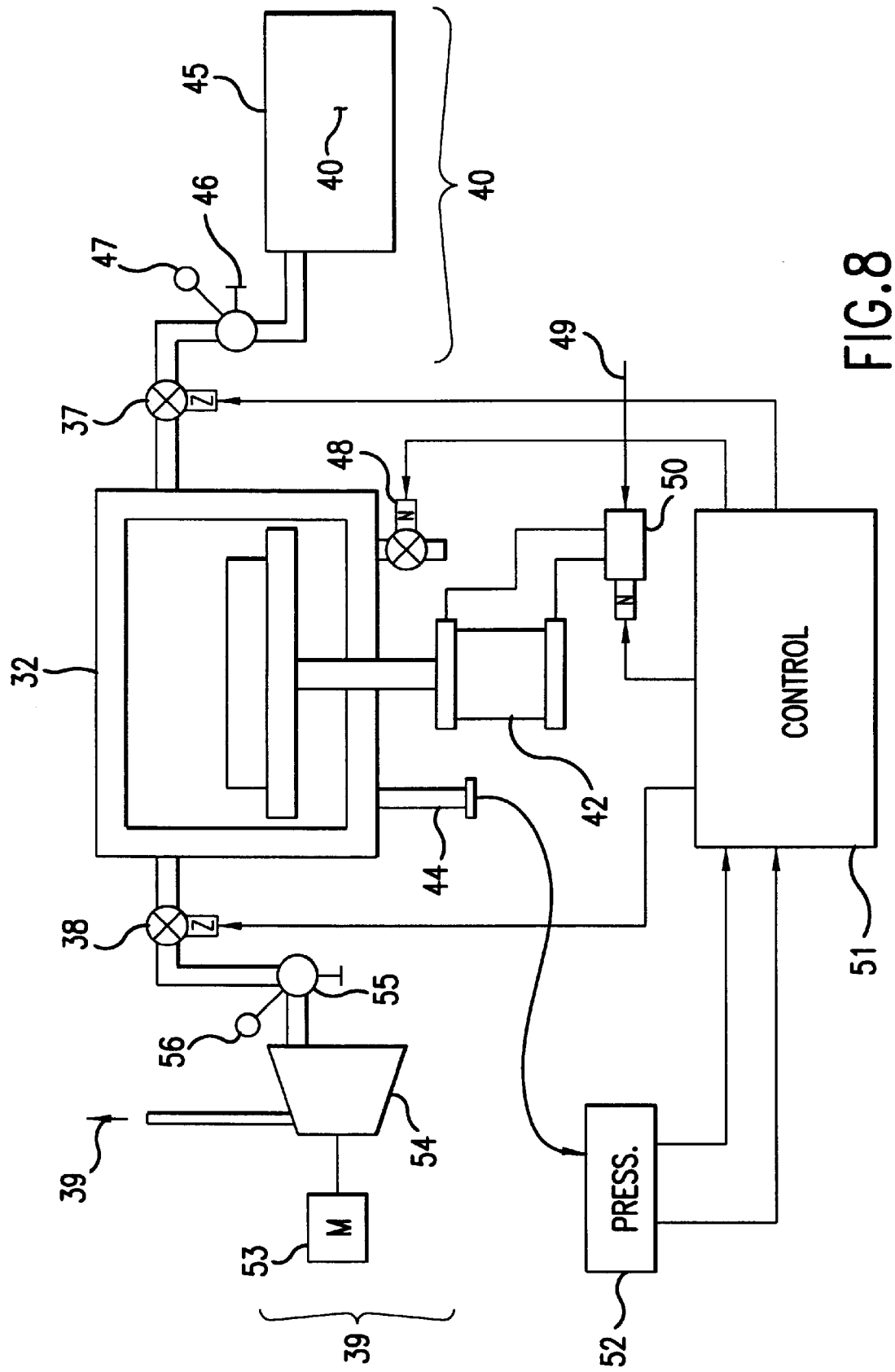
FIG. 8 is a schematic representation of an apparatus suitable for controlling a vacuum and purging oxygen from the composition of the invention.

According to FIG. 8, the inert gas source 40 comprises a gas storage vessel 45, pressure regulator 46 and pressure gauge 47. The chamber 32 is equipped with a pressure release valve 48. A stored source of energy 49 is suitably connected to the motive force device 42 to provide air or hydraulic energy, which can be controlled via valve 50. A means for controlling all aspects and steps of the process 51, such as a programmable logic controller (PLC), connects to the apparatus via control valves 37, 38, 50, and a pressure controller/display mechanism 52, which is associated with the pressure transducer 44. Vacuum source 39 comprises motor 53, vacuum pump 54, vacuum regulator 55, and vacuum gauge 56.

4. Sterilization of the Composition

Formulations of the invention can be aseptically filled or terminally sterilized by a variety of sterilization techniques. Exemplary sterilization techniques useful for preparing the compositions include, but are not limited to, autoclaving, gamma radiation, and electron beam sterilization techniques. Preferably, the formulations of the invention are terminally sterilized. The preferred technique for terminally sterilizing the formulations is autoclaving.

Suitable conditions for autoclaving the formulations include but are not limited to, terminal sterilization at $F_\circ$ of 8 to $F_\circ$ of 16, which denotes a sterilization cycle run at 121.11° C. for 8 to 16 minutes, respectively, with saturated steam.

5. Stability of the Compositions

The compositions of the present invention provide novel formulations with low levels of oxygen in the solution, which demonstrate improved stability in color and potency of the 1α, 25-dihydroxycholecalciferol active agent.

Generally, terminally sterilized products are prepared in accordance with color standards in accordance with the 1995 U.S. Pharmacopiea/National Formulary, Edition No. 23, pages 1779–1780 and 1860–1861. A composition of the invention will typically exhibit a color value of less than about 100 APHA units when measured immediately after container sealing. A preferred composition has a color value of less than about 400 APHA units when stored for three months at a temperature of about 40° C.

Potency levels of the 1α, 25-dihydroxycholecalciferol active agent typically measure from about 90% to about 120% of the formulation during the shelf life of the product. Typically the product shelf life is from about 12 months to about 18 months. Compositions, unit dose systems, and products made by the claimed process can be prepared to have the potency and color values as described above.

The following Example is provided to illustrate the formulations of the invention and is not intended to limit the scope of the invention in any way.

EXAMPLE 1

A calcitriol aqueous solution with the following composition was prepared:

TABLE 2

| Ingredient | Amount per ml |
| --- | --- |
| Calcitriol | 2 mcg |
| Polysorbate 20 | 4 mg |
| Sodium ascorbate | 2.5 mg |
| Water | q.s. |

The formulation was prepared as follows:

1α, 25-dihydroxycholecalciferol (5.75 mg) was accurately weighed in a nitrogen purged glove box and quantitatively transferred into 100 g of polysorbate which was preheated to 65° C. The nitrogen purge was continued in the glove box while mixing, until all the 1α, 25-dihydroxycholecalciferol powder was dissolved in polysorbate. The 1α, 25-dihydroxycholecalciferol concentrate was kept at 5° C. with nitrogen headspace protection and light protection.

To 900 ml of water for injection, was added and dissolved 2.5 mg of sodium ascorbate while maintaining nitrogen sparge in the solution. The nitrogen sparge was switched to nitrogen blanket and maintained for the entire process. Then 2.0 mg of polysorbate was added with mixing. Accurately weighed 2.0 g of 1α, 25-dihydroxycholecalciferol concentrate in polysorbate, 575 mcg/g was added into the solution with gentle mixing. The solution was added quantum sufficiat (q.s.) with water for injection to obtain a 1 L final volume. The solution was mixed gently until uniform. The pH of the solution was adjusted to 8.3–8.7 with addition of either hydrochloric acid or sodium hydroxide.

The solution was filled into amber vials with nominal fill of 1.25 ml per vial via the process previously described in the specification. The oxygen content in the headspace of the container measured immediately after sealing the container was 0.4% by GC (Shimadzu, model GC-17A). After sealing, the vials were terminal sterilized. The pH of the composition was about 7.0. Calcitriol potency, color and aluminum values of the sample were tested at initial, 3 months stored inverted at 40° C. and 9 months stored inverted at 25° C. The potency was tested by using HPLC (Hewlett Packard model, HPLC 1100), the color data were generated on a Gardener colorimeter (BYK Gardener Color Spectrophotometer) and a graphite furnace atomic absorption spectrometer (Perkin Elmer model 4110ZL) was used in the aluminum testing utilizing methodologies known or readily developed by those skilled in the art. The results are presented in Table 4.

TABLE 4

| Time of testing | Potency % | Aluminum, ppb | Color, APHA unit |
| --- | --- | --- | --- |
| Initial | 111 | 82 | 41 |
| 3M, 40° C., inverted | 105 | 218 | 193 |
| 9M, 25° C., inverted | 108 | — | 278 |

The samples showed a stable aqueous formulation for calcitriol that does not contain a buffer and a chelating agent. The formulation was sterilized by autoclave and contained only a trace amount of aluminum in the sterile solution.

EXAMPLE 2

A calcitriol solution with the same composition as in Example 1 was prepared and filled into vials with nominal fill 1.25 ml. The headspace oxygen content in the vials was controlled at different levels by the process described in this invention. The headspace oxygen content was measured immediately after sealing the vials. Calcitriol potency and color were measured at initial and 3 months stored at 40° C. The test data are summarized in Table 5.

TABLE 5

| Headspace | Potency (%) Initial | Potency (%) 3 months at 40° C. | Color, APHA units Initial | Color, APHA units 3 months at 40° C. |
| --- | --- | --- | --- | --- |
| 0.2% Oxygen | 115 | 111 | 11 | 234 |
| 0.5% Oxygen | 117 | 110 | 27 | 269 |
| 1% Oxygen | 115 | 109 | 24 | 235 |
| 1.5% Oxygen | 116 | 110 | 27 | 364 |
| 2% Oxygen | 116 | 109 | 39 | 401 |
| 4% Oxygen | 117 | 104 | 37 | 495 |

The data in Table 5 demonstrated that calcitriol potency remains stable for the sample vials with headspace oxygen levels less than or equal to 2%. Lower oxygen levels in the headspace correlated with the lower color value developed during storage. At 40° C., 3 months, the color value for the 4% headspace oxygen sample is almost twice as high as that in samples with less than 1% headspace oxygen.

What is claimed is:

1. A stable aqueous solution of 1α, 25-dihydroxycholecalciferol, wherein each milliliter (mL) of the solution consists essentially of:
   a. about 1.0 to about 2.0 microgram (mcg) of 1α, 25-dihydroxycholecalciferol;
   b. 4.0 mg of polysorbate 20;
   c. 2.5 mg of sodium ascorbate;
   d. hydrochloric acid quantum sufficiat (q.s.);
   e. sodium hydroxide q.s.; and
   f. water for injection q.s.,
said solution in a container having no more than about 2.0% of oxygen in the headspace of the container.

2. The stable solution according to claim 1, having 1.0 mcg of 1α, 25-dihydroxycholecalciferol per 1 mL of solution.

3. The stable solution according to claim 1, having 2.0 mcg of 1α, 25-dihydroxycholecalciferol per 1 mL of solution.

4. The stable solution according to claim 2 or 3, wherein the pH of the solution is between about 5.9 and about 8.5.

5. The stable solution according to claim 2 or 3, wherein the pH of the solution is about 7.0.

6. The stable solution according to claim 2 or 3, wherein the solution has less than or equal to about one part per million (1 ppm) of aluminum during the shelf life of the composition.

7. A unit dose system comprising an aqueous solution of 1α, 25-dihydroxycholecalciferol in a sealed vessel, wherein each mL of the aqueous solution consists essentially of:
   a. about 1.0 mcg to about 2.0 mcg of 1α, 25-dihydroxycholecalciferol,
   b. 4.0 mg of polysorbate 20;
   c. 2.5 mg of sodium ascorbate;
   d. hydrochloric acid q.s.;
   e. sodium hydroxide q.s.; and
   f. water for injection q.s.;
said unit dose system having less than or equal to 2.0% of oxygen in the headspace.

8. The stable aqueous solution according to claim 1 or 7, wherein the container is a unit dose vial.

9. The stable aqueous solution according to claim 1, wherein the solution measures a mean color value of less than about 100 APHA units immediately after container sealing.

10. The stable aqueous solution according to claim 1, wherein the composition measures a mean color value of less than about 400 APHA units during the shelf life of the product.

\* \* \* \* \*

UNITED STATES PATENT AND TRADEMARK OFFICE
CERTIFICATE OF CORRECTION

PATENT NO. : 6,051,567
DATED : April 18, 2000
INVENTOR(S) : Kent Abrahamson, Amy N. Anderson and Haiyan Grady It is certified that error appears in the above-identified patent and that said Letters Patent is hereby corrected as shown below:

Col. 14, line 60
 replace "said solution"
 with - -wherein said solution is essentially free of buffer and/or chelating agent,- -.

Col. 14, line 60
 replace "in a container"
 with --in a sealed container--.

Col. 14, line 62
 replace "claim"
 with --Claim--.

Col. 14, line 65
 replace "claim"
 with --Claim--.

Col. 15, line 01
 replace "claim"
 with --Claims--.

Col. 15, line 03
 replace "claim"
 with --Claims--.

Col. 15, line 05
 replace "claim"
 with --Claims--.

UNITED STATES PATENT AND TRADEMARK OFFICE
CERTIFICATE OF CORRECTION

PATENT NO. : 6,051,567

DATED : April 18, 2000

INVENTOR(S) : Kent Abrahamson, Amy N. Anderson and Haiyan Grady

It is certified that error appears in the above-identified patent and that said Letters Patent is hereby corrected as shown below:

Col. 16, line 03
  replace "said unit dose system"
  with - -wherein said solution is essentially free of buffer and/or chelating agent,- -.

Col. 16, line 04
  replace "in the headspace."
  with - -in the headspace of said sealed vessel.- -.

Col. 16, line 05
  replace "claim"
  with - -Claims- -.

Col. 16, line 07
  replace "claim"
  with --Claim--.

Col. 16, line 11
  replace "claim"
  with --Claim--.

Signed and Sealed this

Twenty-second Day of May, 2001

Attest:

NICHOLAS P. GODICI

Attesting Officer

Acting Director of the United States Patent and Trademark Office